United States Patent
Paulekuhn et al.

(10) Patent No.: US 10,591,747 B2
(45) Date of Patent: Mar. 17, 2020

(54) CONTACT LENS INSPECTION METHOD AND SYSTEM

(71) Applicant: Novartis AG, Basel (CH)

(72) Inventors: Steffen Paulekuhn, Grosswallstadt (DE); Susanne Fechner, Grosswallstadt (DE); Sarah Unterkofler, Grosswallstadt (DE); Daniel Kessler, Grosswallstadt (DE); Evgeni Schumm, Constance (DE); Matthias Schwab, Grosswallstadt (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/123,302

(22) Filed: Sep. 6, 2018

(65) Prior Publication Data
US 2019/0072784 A1    Mar. 7, 2019

Related U.S. Application Data

(60) Provisional application No. 62/555,123, filed on Sep. 7, 2017.

(51) Int. Cl.
| | | |
|---|---|---|
| *G01M 11/02* | (2006.01) | |
| *G02C 7/04* | (2006.01) | |
| *H04N 5/232* | (2006.01) | |
| *H04N 5/357* | (2011.01) | |
| *G06T 7/50* | (2017.01) | |
| *H04N 5/225* | (2006.01) | |
| *G01N 21/958* | (2006.01) | |

(52) U.S. Cl.
CPC .............. *G02C 7/04* (2013.01); *G01M 11/02* (2013.01); *G01M 11/0221* (2013.01); *G01M 11/0257* (2013.01); *G01N 21/958* (2013.01); *G06T 7/50* (2017.01); *H04N 5/2254* (2013.01); *H04N 5/23212* (2013.01); *H04N 5/357* (2013.01); *G01N 2021/9583* (2013.01)

(58) Field of Classification Search
CPC .......... G01M 11/0235; G01M 11/0221; G01M 11/081; G01M 11/02; G02C 7/04; H01N 5/23212; H04N 5/265; H04N 5/357; H04N 5/2254; H04N 5/2256; G06T 7/50; G06T 7/557; G01N 21/958; B29D 11/0098
USPC ...................................... 356/124–127, 239.2
See application file for complete search history.

(56) References Cited

U.S. PATENT DOCUMENTS

| | | | | |
|---|---|---|---|---|
| 5,500,732 A | * | 3/1996 | Ebel ................... | G01M 11/0264 356/124 |
| 5,719,669 A | * | 2/1998 | Ross, III .............. | G01B 11/255 356/124 |
| 6,134,342 A | * | 10/2000 | Doke .................. | G01M 11/0264 356/124 |
| 7,990,531 B2 | * | 8/2011 | Clements ........... | G01M 11/0278 356/239.2 |
| 9,253,448 B1 | | 2/2016 | Wang et al. | |
| 2016/0223429 A1 | * | 8/2016 | Fecnher ................ | G01B 11/24 |
| 2019/0072499 A1 | * | 3/2019 | Unterkofler ........ | G01M 11/0257 |

FOREIGN PATENT DOCUMENTS

| | | |
|---|---|---|
| GB | 2433782 A1 | 7/2007 |
| WO | WO2015036432 A1 | 3/2015 |

\* cited by examiner

*Primary Examiner* — Hoa Q Pham
(74) *Attorney, Agent, or Firm* — Patrick M. Ryan

(57) ABSTRACT

Disclosed is an inspection and system method and system for determining the orientation of a contact lens on a lens support, particularly in an automated contact lens manufacturing line.

9 Claims, 2 Drawing Sheets

CONTACT LENS INSPECTION METHOD AND SYSTEM

This application claims the benefits under 35 USC 119(e) of U.S. provisional application Ser. No. 62/555,123 filed on Sep. 7, 2017, incorporated herein by reference in its entirety.

FIELD

The invention relates to a contact lens inspection method and system as to whether they are properly oriented on a lens support, particularly in an automated contact lens manufacturing line.

BACKGROUND

Contact lenses from a wide range of materials are nowadays produced in great volumes in highly automated manufacturing lines. To ensure top quality of the manufactured contact lenses, the final contact lenses are optically inspected prior to packaging. Because contact lenses are intended for use on the eye, great care must be taken to make sure that the lenses meet strict quality standards.

In order to ensure the quality of the contact lenses, they are transferred into an inspection system which evaluates if the considered contact lens meets the strict requirements according to set parameters. For reasons of simplifying the evaluation of the parameters, the criteria generally are set for a contact lens which is properly oriented on the lens holder. A lens holder may, for example, be a bottom of an inspection cuvette. A properly oriented contact lens means that the contact lens is oriented in such a manner on the lens holder, that the curved surface of the contact lens is oriented towards the surface of the lens holder bearing the contact lens during the inspection step. In case of a properly oriented contact lens, the lens edge is oriented upwards in the opposite direction away from the bearing surface of the lens holder. In case the contact lens is oriented upside-down, the lens edge is oriented towards the bearing surface of the lens holder. In case the contact lens is not properly oriented on the bearing surface of the lens holder (upside-down orientation), the evaluation of the considered contact lens whether or not the contact lens meets the strict quality requirements cannot simply be performed using set parameter values. Additionally, detecting an upside-down oriented contact lens may trigger additional measures in the subsequent steps, such as reorienting the contact lens.

Accordingly, there is a need for a reliable inspection method and system which detects whether the contact lens is properly oriented on the lens holder. A contact lens inspection method and system shall be provided, which is relatively simple, and which provides accurate results in particular with regard to the detection of upside-down oriented contact lenses. The contact lens inspection method and system shall be in particular capable of being combined with and integrated into an automated manufacturing line for contact lenses.

SUMMARY

In the following, whenever features are combined with the term "or", the term "or" is to be understood to also include "and" unless it is evident from the specification that the term "or" must be understood as being exclusive. For example, the term "determining a transition from the fluid to the front surface or the back surface of the ophthalmic lens" is to be understood to include cases in which only the transition to the front surface is determined, furthermore to include cases in which only the transition to the back surface is determined, as well as cases in which both the transition to the front surface and to the back surface is determined.

The present invention suggests a method for determining the orientation of a contact lens on a lens support comprising the steps of:
providing a contact lens having a lens center and a sagittal height,
providing a lens support,
arranging the contact lens on the lens support,
providing a camera system having a depth of field of less than the sagittal height,
illuminating the contact lens arranged on the lens support with a light beam,
focusing the camera system to a set focus corresponding to the expected position of the lens center of the properly oriented contact lens arranged on the lens support with the lens center of the properly oriented contact lens on the lens support being within the depth of field of the focused camera system,
producing an image of the contact lens,
scanning the image of the contact lens in at least one image portion of a predetermined size;
determining the image defocus of the at least one image portion,
determining the orientation of the contact lens from the image of the contact lens by comparing the determined image defocus with a predetermined threshold.

In some embodiments of the method according to the invention, the step of providing a camera system comprises providing a camera system having a depth of field of up to 70%, particularly up to 50%, more particularly up to 40% of the sagittal height.

In some further embodiments of the method according to the invention, the step of determining the image defocus is performed by determining the image blur and the step of determining the orientation of the contact lens by comparing the determined image blur with a predetermined threshold.

In still some further embodiments of the invention, the step of determining the image blur is performed by determining the image noise and determining the orientation of the contact lens by comparing the determined image noise with a predetermined threshold.

In some specific embodiments of the method according to the invention, determining the image noise of the at least one image portion is performed by applying a Wiener filter or a Fourier transform.

In still some further embodiments of the method according to the invention, the step of producing an image of the contact lens comprises producing an orthographic image of the contact lens.

In some specific embodiments of the method according to the invention, the step of producing an image of the contact lens comprises using a bright field imaging unit.

In some further embodiments of the method according to the invention, the step of producing an image of the contact lens comprises using a dark field imaging unit.

A further aspect of the invention is directed to a contact lens inspection system, in particular for soft contact lenses, comprising:
a light source being configured to illuminate a contact lens;
a camera system having an objective lens and an electronic sensor, the camera system being configured to have a depth of field of less than the sagittal height of the lens to be inspected, and being arranged to produce an image of the contact lens on the electronic sensor;

an scanning and evaluation unit configured to scan at least one image portion of a predetermined size to determine the image defocus in the at least one image portion and configured to compare the determined image defocus with a predetermined threshold to determine whether the contact lens is properly oriented.

In some embodiments of the contact lens inspection system according to the invention, the camera system has a depth of field of up to 70%, particularly up to 50%, more particularly up to 40% of the sagittal height.

In some embodiments of the contact lens inspection system according to the invention, the scanning and evaluation unit is configured to determine the image blur and to determine the orientation of the contact lens by comparing the determined image blur with a predetermined threshold.

In some further embodiments of the contact lens inspection system according to the invention, the scanning and evaluation unit is configured to determine the image noise and to determine the orientation of the contact lens by comparing the determined image noise with a predetermined threshold.

In some specific embodiments of the contact lens inspection system according to the invention, the scanning and evaluation unit is configured to apply a Wiener filter or a Fourier transform to the at least one image portion.

In some embodiments of the contact lens inspection system according to the invention, the objective lens comprises a telecentric lens.

In some specific embodiments of the contact lens inspection system according to the invention, the camera system is a bright field imaging unit.

In some further embodiments of the contact lens inspection system according to the invention, the camera system is a dark field imaging unit.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

By taking an image of the contact lens and by scanning the image for the defocus level, it can be determined whether the contact lens is properly oriented. When the contact lens is properly oriented, the lens center will be located within the depth of field range at the set focus and will therefore represent the contact lens and its boundaries, for example, sharply, thus resulting in low image defocus. On the contrary, when the contact lens is oriented upside-down, the area around the lens center will be out of focus of the camera system and resulting in high image defocus.

Hence, the contact lens inspection method and system of the present invention allow for reliable and simple identification of upside-down oriented contact lenses and may be combined with normal inspection of contact lenses, for example for determining cosmetic defects. The lens inspection system preferably is fully automated and can be easily integrated into inspection stations of automated manufacturing lines in which contact lenses are inspected, for example, for accuracy in size, surface defects, tears, peripheral ruptures and inclusions such as bubbles or other inclusions, as well as small defects at the edges of the contact lenses. Typically, contact lenses have a sagittal height in the range of from 3 mm to 5 mm, in particular in the range of from 3.5 mm to 4.5 mm. In particular, the image produced of the contact lens is an electronic image which may then readily be evaluated for the determination of the image defocus.

The contact lens may, in a particular embodiment of the method according to the invention, comprise a structural pattern. The materials for the contact lenses, in particular soft contact lenses, may comprise structural pattern either on the surface or comprised in the contact lens. Such structural pattern may be inherently comprised on or in the contact lens or intentionally applied to or mixed into the material of the contact lens. These structural pattern further increase the accuracy of the method according to the invention.

For example, structural pattern included in the contact lens may be composed of small amounts of coloring pigments giving the final contact lenses a slightly colored, for example bluish, appearance. This very decent coloring of the contact lens which is not noticed when the contact lens is worn on the eye assists the wearer in identifying the contact lens in the storage solution (e.g. saline) contained in the package and makes it easier to grab the lens for placing it on the fingertip and onto the eye. The coloring pigments are homogeneously distributed in the contact lens material and when an electronic image of the contact lens is produced, the electronic image comprises a structural pattern generated by the pattern of the homogeneously distributed pigments when the camera system is configured to have a depth of field comprising plane at which of the contact lens is expected when properly oriented. When the contact lens is properly oriented, an image of the contact lens shows a clear structural pattern, for example a clear fine-structure of the pigments with a homogeneous distribution. When the contact lens is oriented upside-down, the camera is focused on the expected level of a properly oriented contact lens and the fine-structure of the contact lens inspected being located outside of the focus of the camera system is represented as a defocused image which defocus level is subsequently evaluated.

While it is of course possible to scan the entire digital image of said contact lens, it may be preferable to scan only a portion of the image of the contact lens, in particular the central portion of the contact lens, in order to determine whether the contact lens is properly oriented. This enhances the speed and the accuracy of the determination of the orientation of the contact lens and, as a consequence, the efficiency of the evaluation by the lens inspection of the compliance of the contact lens to strict quality standards. Within the scanned portion, the determination of the defocus level is performed in sections of a predetermined size suitable for this determination. In particular, the sections have a size such that the sections are located within the depth of field of the camera system when the contact lens is properly oriented. Such section can have different sizes and geometric orientation, and can be regarded as a window in which the respective determination of the image defocus level is performed.

The camera system may in particular have a depth of field of up to 70%, particularly up to 50%, very particularly up to 40% of the sagittal height of the contact lens for enhanced determination of the orientation of the contact lens. In particular, the camera system may have a depth of field of up to 2 mm, particularly up to 1.5 mm, very particularly up to 1 mm.

Determining the image blur is a particularly well suited method for determining the image defocus level. If the contact lens is properly oriented, the contact lens boundaries or structural pattern in or on the contact lens, for example, will be well defined, and the representation of the contact lens in the considered image portion will be sharp and the image will have a low blur level. If the contact lens is oriented upside-down, the center of the contact lens will be out of focus as it will be located outside of the depth of field of the camera system, the representation of the contact lens in the considered image portion will be blurry.

In particular, when the contact lens comprises a structural pattern, the representation of the structural pattern will have a high degree of blur when the contact lens is upside down.

In particular, the determination of the image noise is a particularly efficient method particularly well suited for contact lenses comprising a structural pattern. The structural pattern will be clearly represented in the image portion considered when the contact lens is properly oriented. Determining the image noise in such an image portion will result in a high image noise value as the sharp fine-structure representation in the image portion will result in high luminosity variation from one location to an adjacent location in the image portion. When the lens center is located outside of the focus of the camera system, a blurry representation of the structural pattern will result in low image noise value.

A telecentric lens is a particularly suitable objective lens of a camera for producing an orthographic image and has its entrance pupil at infinity. Thus, irrespective of the position of the contact lens the image of the contact lens will have a constant magnification and produces an orthographic image of the contact lens. The electronic sensor onto which the orthographic image impinges to form a digital orthographic image, may be a CCD-sensor, a CMOS-sensor, or any other suitable sensor.

For example, each of the sections may be of rectangular or circular shape. The section may have a size of 200 pixels of the CCD-sensor. If the defocus level within this section exceeds a predetermined threshold value, this is a clear indication that the inspected contact lens is oriented upside-down.

Advantages were already described for the method for determining the orientation of a contact lens on a lens support and apply to the contact lens inspection system in an analogous way.

BRIEF DESCRIPTION OF THE DRAWINGS

Further details and advantages of the invention will become apparent from the following description of exemplary embodiments of the invention with the aid of the drawings, in which:

FIG. 1b shows a plan view of the properly oriented soft contact lens of FIG. 1a;

FIG. 2b shows a plan view of the upside-down oriented soft contact lens of FIG. 2a;

DETAILED DESCRIPTION

Figure 1A:
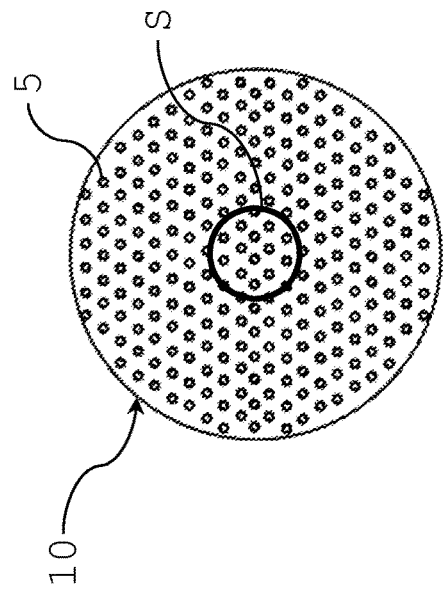
FIG. 1a shows a side elevational view of a properly oriented soft contact lens.

FIG. 1a shows a properly oriented contact lens 1 with a convex surface which is oriented towards the bearing surface of the lens holder 3. The central part of the contact lens 1 is situated within the depth of field 4 of the camera system configured for imaging at least part of the properly oriented contact lens 1 comprising the center of the contact lens when the contact lens rests against the bearing surface of the lens holder 3. The camera system has a depth of field 4 of 2 mm. Ideally, the center of the physical contact lens is located at the focal plane of the camera system, which is the plane at which the camera system focuses. The depth of field is distributed on both sides of the focal plane.

Figure 1B:
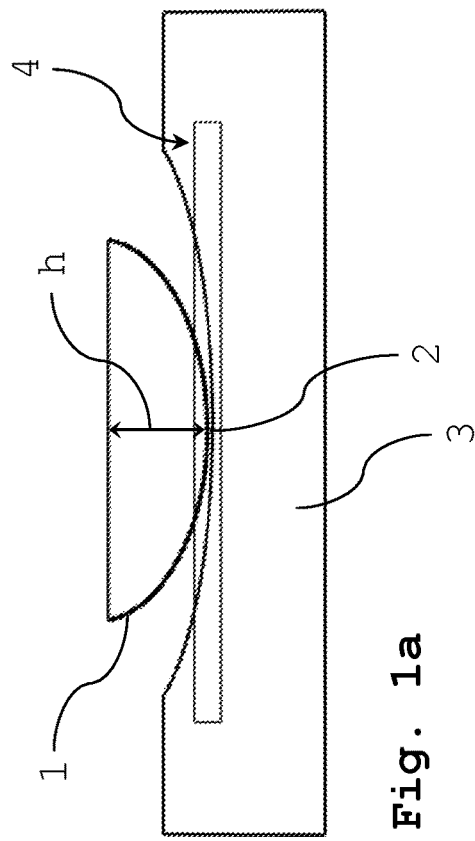

FIG. 1b shows an image 10 of a plan view of the properly oriented contact lens of FIG. 1a. Illuminated with collimated light having parallel light rays the fine-structure, for example of the coloring pigments, becomes visible on the imaged view. As is schematically shown in FIG. 1b the contact lens shows a sharp visual distinction of the granular fine-structure 5 of the surface of the contact lens. The granular structure 5 is homogeneously distributed in the contact lens 1. The image 10 of the contact lens may be then scanned in at least one image portion S of a predetermined size for image defocus, in particular image blur or image noise, as explained below.

Figure 2A:
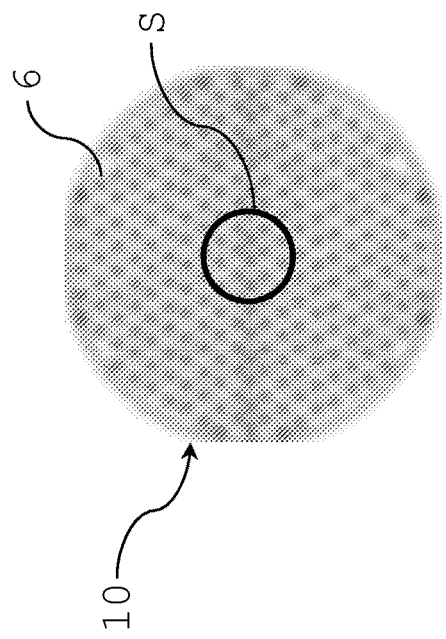
FIG. 2a shows a side elevational view of the soft contact lens of FIG. 1a, in an upside-down orientation.

FIG. 2a shows a contact lens 1 in the upside down orientation with a convex surface which is oriented away from and the lens edge is oriented towards the bearing surface of the lens holder 3. The central part of the contact lens 1 is situated outside of the depth of field 4 of the camera system. The center of the physical contact lens is located outside of the focal plane of the camera system.

Figure 2B:
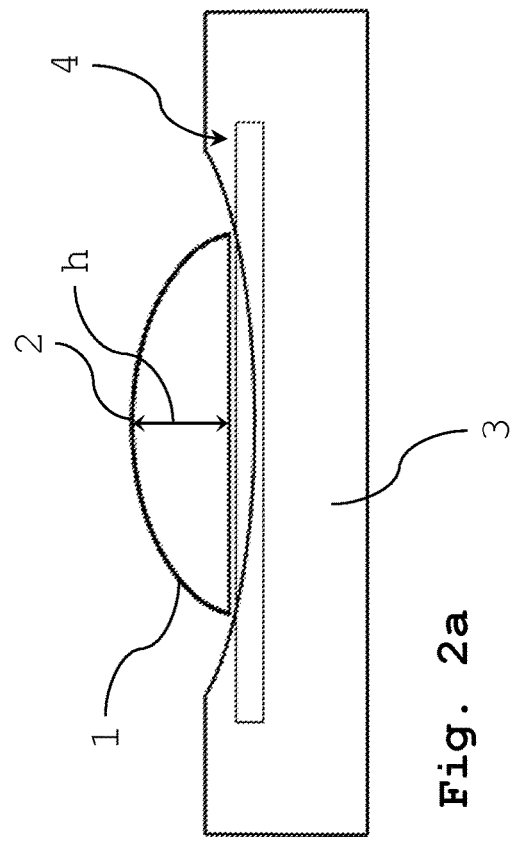

FIG. 2b shows an image 10 of a plan view of the upside-down soft contact lens. As is schematically shown in FIG. 2b the fine-structure 6 of the pigments is not distinguishable any more due to the heavy blur as the picture is taken outside of the depth of field of the camera system. The image 10 of the contact lens may be then scanned in at least one image portion S of a predetermined size for image defocus, in particular image blur or image noise, as explained below.

A sharp image as shown in FIG. 1b results in well determined structures represented on the digital image 10 and may be compared to high level of image noise. When the image taken is not sharp as for example in FIG. 2b, the resulting blurry image 10 will appear greyish and the structure from the contact lens will vanish more and more with increasing defocus of the camera system with respect to the physical center of the contact lens.

Figure 3:
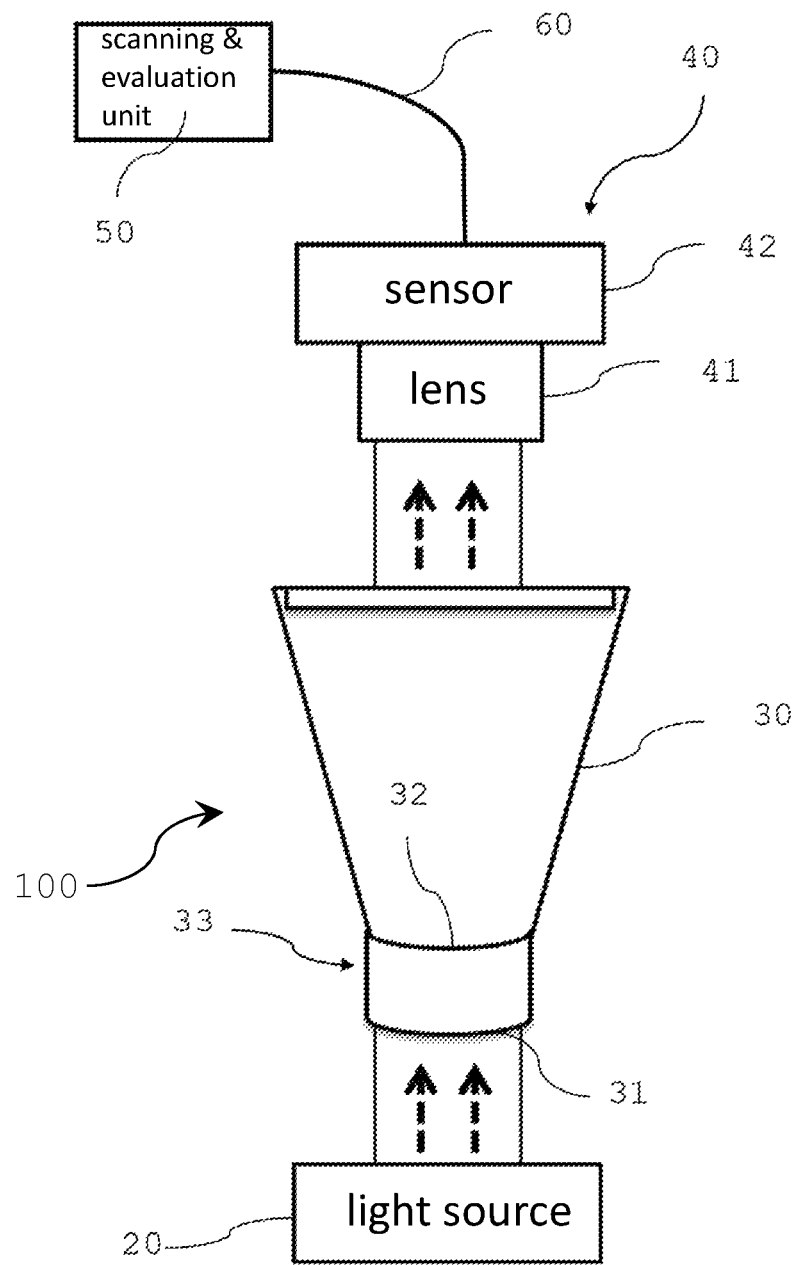
FIG. 3 shows an embodiment of a contact lens inspection system according to the invention.

FIG. 3 shows a schematic view of an embodiment of a contact lens inspection system 100 according to the invention. The contact lens inspection system 100 comprises a light source 20 for illuminating a contact lens, in particular a soft contact lens 1, which is held in a container 30 in liquid, for example water. The light source 20 is arranged at a first longitudinal end of the container 30 near the container bottom 33, and illuminates the soft contact lens with collimated (parallel) light. Container bottom 33 is transparent to the collimated light impinging thereon, and in the embodiment has a slightly convex outer surface 31. The soft contact lens 1 may be supported inside the container 30 on a slightly concave inner surface 32 of container bottom 33, this concave inner surface 32 forming a support bearing the soft contact lens 1. The other longitudinal end of the container 30 can be either open, or may be provided with a lid which is transparent with respect to the collimated light impinging on and traversing the container 30. At that longitudinal end of the container 30 opposite to the end where the light source 20 is arranged, there is arranged a camera system 40 comprising an objective lens 41 and an electronic sensor 42, for example a CCD-sensor or CMOS-sensor.

The camera system 40 has a telecentric lens system 41 as objective which allows for orthographic bright field or dark field orthographic imaging of the contact lens 1 in the container 30. An orthographic image of the soft contact lens 1 is produced on the electronic sensor 42.

The telecentric lens system is in particular a combination of a lens objective from Schneider with a focal length f=40 or f=35 and an Achromat front lens with a focal length f=100. The sensor is from Basler of the type A102f or Aviator.

The electronic sensor 42 converts the orthographic image into a digital orthographic image. The telecentric lens for producing an orthographic image of the contact lens has its entrance pupil at infinity. Thus, irrespective of the position of the soft contact lens 1 within the container 30, the image of the soft contact lens 1 will have a constant magnification, thus producing an orthographic image which is then converted by the electronic sensor into a digital orthographic image. The camera system 40 is connected via a data line 60 with a scanning and evaluation unit 50.

In the scanning and evaluation unit 50, the central portion of the digital orthographic image of the soft contact lens 1 is electronically processed and the image noise in the central portion S evaluated.

The evaluation of the noise is particularly performed using a Wiener filter which allows for a quantification of the image noise. The Wiener filter is a practical embodiment for simple image noise evaluation. To this end, a section of predetermined size of the central portion of the image is scanned. For example, the section may be a circle having a radius of 200 pixel around its center. Applying the Wiener filter will result in a filtered image and an image representing the image noise. The luminosity of each pixel is then evaluated. The intensity of the luminosity of each pixel may then be multiplied by a predetermined factor for an optimized subsequent evaluation of the image noise. Alternatively to the Wiener filter, a Fourier transform may also be applied to the frequencies present in the digital images. A blurry image will result in low amount of high frequencies present in the image.

The noise image as processed by the Wiener filter is subsequently evaluated by applying for example a L2 Norm of square-summable sequences by calculating the square root of the integral of the squared intensity values for the luminosity over the considered section and resulting in a L2 value. The image noise is directly correlated to the L2 value and higher image noise results in a higher L2 value.

The L2 value is compared with a predetermined threshold value in order to determine whether the inspected soft contact lens 1 within said container is properly oriented or upside-down. If the soft contact lens 1 is found to be in upside-down orientation, an action may be initiated to have the soft contact lens 1 rotated to its proper orientation prior to the soft contact lens 1 being further inspected.

Although the invention has been described with the aid of specific embodiments, it is evident to the person skilled in the art that this embodiment has been described by way of example only, but representing the general inventive concept, and that various changes and modifications can be made without departing from the technical teaching underlying the invention. Therefore, the invention is not intended to be limited by the embodiment described, but rather is defined by the appended claims.

The invention claimed is:

1. A method for determining the orientation of a contact lens on a lens support comprising the steps of:
   providing a contact lens having a lens center and a sagittal height (h),
   providing a lens support,
   arranging the contact lens on the lens support,
   providing a camera system having a depth of field of less than the sagittal height (h),
   illuminating the contact lens arranged on the lens support with a light beam,
   focusing the camera system to a set focus corresponding to the expected position of the lens center of the properly oriented contact lens arranged on the lens support with the lens center of the properly oriented contact lens on the lens support being within the depth of field of the focused camera system,
   producing an image of the contact lens,
   scanning the image of the contact lens in at east one image portion (S) of a predetermined size;
   determining the image defocus of the at least one image portion (S),
   determining the orientation of the contact lens from the image of the contact lens by comparing the determined image defocus with a predetermined threshold (T).

2. The method according to claim 1, wherein the step of providing a camera system comprises providing a camera system having a depth of field of up to about 40% of the sagittal height (h).

3. The method according to claim 2, wherein the step of determining the image defocus is performed by determining an image blur level and the step of determining the orientation of the contact lens is performed by comparing the determined image blur with a predetermined threshold (T).

4. The method according to claim 1, wherein the step of determining the image defocus is performed by determining an image blur level and the step of determining the orientation of the contact lens is performed by comparing the determined image blur with a predetermined threshold (T).

5. The method according to claim 4, wherein the step of determining the image blur is performed by determining an image noise level and determining the orientation of the contact lens is performed by comparing the determined image noise with a predetermined threshold (T).

6. The method according to claim 5, wherein determining the image noise of the at least one image portion (S) is performed by applying a Wiener filter or a Fourier transform.

7. The method according to claim 1, wherein the step of producing an image of the contact lens comprises producing an orthographic image of the contact lens.

8. The method according to claim 1, wherein the step of producing an image of the contact lens comprises using a bright field imaging unit.

9. The method according to claim 1, wherein the step of producing an image of the contact lens comprises using a dark field imaging unit.

* * * * *